United States Patent [19]

Ohki et al.

[11] Patent Number: 5,304,544

[45] Date of Patent: Apr. 19, 1994

[54] ANTI-PLANT PATHOGEN MATERIALS AND METHODS

[75] Inventors: Satoshi Ohki, Miharamachi, Japan; Tsuneya Ohno; Masaki Terada, both of Boston, Mass.

[73] Assignee: Nissin Shokuhin Kabushiki Kaisha, Osaka, Japan

[21] Appl. No.: 862,335

[22] Filed: Apr. 2, 1992

[51] Int. Cl.$^5$ .................... A61K 31/70; A61K 35/78; A01N 3/02
[52] U.S. Cl. .................................. 514/23; 424/195.1
[58] Field of Search ................... 424/195.1; 514/23; 71/66

[56] References Cited

FOREIGN PATENT DOCUMENTS

WO91/18984  12/1991  PCT Int'l Appl. .......... C12N 15/29

OTHER PUBLICATIONS

Kopp et al., *Plant Physiol.*, 90, 208–216 (1989).
Matthews, *Plant Virology*, Chapter 16, Academic Press, Inc., San Diego (1991).
Pearce et al., *Science*, 253, 895–898 (1991).
Shohara et al., *Ann. Phytopath. Soc. Japan*, 44, 619–625 (1978).
Merck Index, 9th ed., 1976, p. 225, #1773.

*Primary Examiner*—John W. Rollins
*Attorney, Agent, or Firm*—Marshall, O'Toole, Gerstein, Murray & Borun

[57] ABSTRACT

Disclosed are compositions comprising caramel that have anti-plant pathogen activity. Methods of treatment of higher plants with the compositions to inhibit both the infection of plants by pathogens and the multiplication of pathogens in infected plants are also provided. Compositions according to the present invention are particularly suited for use against plant viruses such as cucumber mosaic virus.

10 Claims, No Drawings

ANTI-PLANT PATHOGEN MATERIALS AND METHODS

BACKGROUND

The present invention relates generally to anti-plant pathogen materials and methods of use, and ore particularly, to anti-plant virus compositions and methods for their use.

Plant fungal and viral disease losses worldwide have been estimated to be as high as sixty billion dollars per year. Examples of plant viruses that contribute to significant losses in crop productivity are cucumber mosaic virus, tobacco mosaic virus and zucchini mosaic virus. The economic importance and control of plant viruses is discussed in Matthews, *Plant Viruses*, Chapter 16, Academic Press, Inc., San Diego (1991).

Considerable effort has been expended by the agricultural industry and by academic researchers in developing materials and methods for inhibiting infection by and/or reducing deleterious effects of plant pathogens. Kopp et al., *Plant Physiol.*, 90, 208–216 (1989) describe a glucan preparation obtained from a fungus which serves as an inducer of resistance in tobacco to viruses (tobacco mosaic virus, tomato black ring virus and alfalfa mosaic virus) from three taxonomic groups. Pearce et al., *Science*, 253, 895–898 (1991) describe a native peptide, "systemin," that stimulates production of proteinase inhibitors (defensive proteins made in plants in response to wounding, for example, by insects) in tomatoes. Patent Cooperation Treaty (PCT) published application number WO 91/18984 describes methods for identifying and purifying plant proteins with anti-pathogenic (and particularly anti-fungal) activity.

Criteria determining the potential success of an anti-pathogenic composition in preventing or controlling plant diseases, especially viral diseases, include: whether the composition damages the plant; whether the composition affords systemic protection to the plant; whether the composition retains its activity for a reasonable length of time; whether the composition may be produced on a large scale at an economic price; and whether the composition would pass, or not be subject to, food and drug environmental protection regulations. So far there have been no commercially available antiviral chemicals that satisfy the foregoing criteria and there thus continues to exist a need in the art for new anti-plant pathogen compositions.

SUMMARY OF THE INVENTION

The present invention provides compositions having anti-plant virus activity and satisfying the foregoing criteria for successful anti-pathogenic materials. Antiviral compositions according to the invention preferably comprise a glucose caramel combined with a physiologically acceptable diluent, adjuvant or carrier. More preferably, the compostions comprise a Type IV caramel, i.e., one derived from the reaction of ammonia, glucose and sulfide. A presently preferred caramel is available under the designation TB from the Amano Jitsugyo Company (Fukuyama, Hiroshima, Japan). The concentration of caramel in compositions of the present invention may range from 1 µg/ml to 50 mg/ml, with a particularly useful concentration being 10 µg/ml. A presently preferred diluent for caramel compositions is 0.1M phosphate buffer at pH 7.0.

DETAILED DESCRIPTION

Caramel compositions according to the present invention are particularly useful in the treatment of plants susceptible to infection by or previously infected with cucumber mosaic virus (CMV). Thus, both treatment to inhibit the infection of plants by CMV virus and treatment to inhibit the multiplication of the virus in infected plants are contemplated by the present invention. Treatment to inhibit other viruses and fungi is contemplated as well.

The treatment of plants according to the invention may involve spraying a caramel composition on the leaves of plants, adding the composition to the water supply of the plants, or in the case of plants grown by tissue culture, adding the composition to the culture media. Treatment of both monocotyledonous and dicotyledonous higher plants is contemplated.

Other aspects and advantages of the present invention will be appreciated upon consideration of the following detailed description of presently preferred embodiments thereof.

Caramel compositions were tested for their ability to inhibit the infection of dicotyledonous *Vigna ungiculata* subspecies sesquipedalis plants by CMV. CMV is RNA virus transmitted mainly by aphids, which causes serious disease in a wide variety of crops including, for example, tomato, cucumber, zucchini, muskmelon, sweet potato, sugar beet and tobacco. The virus is carried by perennial ornamental plants such as the violet and the gladiolus. CMV is a plant virus of worldwide economic significance.

Infectivity Inhibition Assay

A composition of 10 µg/ml caramel (TB Amano Jitsugyo Company) in 0.1M phosphate buffer pH 7.0 was prepared. A small calligraphy brush was used to apply a coat of the caramel composition to a first leaf of two-leaf *Vigna unguiculata* seedlings (Takii Seed Company, Kyoto, Japan), either two hours before infection of the seedlings with CMV [strain pepo obtained from the College of Agriculture, University of Osaka Prefecture, Osaka, Japan, and described in *Annals of the Phytopathological Society of Japan*, 44, 619–625 (1978)], contemporaneously to infection, or two hours after infection. Control seedlings were either totally untreated or treated only with 0.1M phosphate buffer pH 7.0 on a first leaf. The composition was applied to the front of the leaf of some seedlings and the back of the leaf of others. The second leaf of both the treated and control seedlings was not treated with the caramel composition or with buffer.

The front of both leaves of both the treated and control seedlings was then infected with CMV by a method similar to that described in Kopp et al., supra. Leaves were inoculated with virus by abrasion of the leaf surface in the presence of a suspension containing purified CMV. The infected seedlings were cultivated in a controlled environment at 25° C. for 3 days to allow the infection to develop. The number of infectious spots, equivalent to viral plaques, was then counted for each leaf of each seedling. The results of the assay are presented below in Table 1, wherein each number of infectious spots for treated and untreated leaves represents the average of the numbers of infectious spots obtained for ten seedlings. Totally untreated control seedlings displayed more than 250 infectious spots per leaf.

TABLE 1

| Concentration (ug/ml) of Caramel in Buffer | Treatment in Relation to Time of Infection | Side of Leaves Treated | # of Infectious Spots | |
|---|---|---|---|---|
| | | | Treated Leaves | Untreated Leaves |
| 10 | ≧2 hours before | Front | 8 | 29 |
| 0 | ≧2 hours before | Front | 283 | 299 |
| 10 | ≧2 hours before | Back | 32 | 71 |
| 0 | ≧2 hours before | Back | 173 | 187 |
| 10 | Concurrent | Front | 49 | 81 |
| 0 | Concurrent | Front | 217 | 238 |
| 10 | Concurrent | Back | 28 | 28 |
| 0 | Concurrent | Back | 164 | 187 |
| 10 | ≧2 hours after | Front | 20 | 50 |
| 0 | ≧2 hours after | Front | 194 | 198 |
| 10 | ≧2 hours after | Back | 50 | 56 |
| 0 | ≧2 hours after | Back | 248 | 231 |

The results presented in Table 1 indicate that caramel compositions of the present invention inhibit the infectivity/multiplication of CMV. Significantly, the protection afforded the plants by the compositions is systemic, as is evidenced by the reduced number of infectious spots on the untreated second leaf of the seedlings wherein the first leaf was caramel-treated. Also highly significant was the fact that protection was also afforded the plants that were treated with the caramel compositions after infection with CMV. No damage to the caramel-treated leaves/plants was noted in comparison to the buffer-treated leaves/plants. In a collateral experiment, some adverse effects on seedling growth were noted when a caramel concentration of 100 $\mu$g/ml was employed.

These results, along with the fact that caramel is already a commercial product produced on a large scale that meets food and drug regulations, indicate that the caramel compositions of the present invention satisfy the criteria for anti-pathogenic compositions likely to be successful in preventing or controlling the viral infection of plants.

While the present invention has been described in terms of preferred embodiments, it is understood that numerous modifications and variations will occur to those skilled in the art. For example, compositions according to the invention may be effective against viruses other than CMV including tobacco mosaic virus and zucchini yellow virus, and may protect plants other than *Vigna unguiculata* seedlings including tomato, cucumber and tobacco plants. The compositions may comprise diluents such as water and liquid fertilizer, and may be combined with other agents having anti-plant pathogen activity.

We claim:

1. A method for inhibiting the infection of plants by viruses comprising the step of treating said plants with a composition comprising from 1 $\mu$g/ml to 50 mg/ml caramel and a physiologically acceptable diluent, adjuvant or carrier.

2. The method recited in claim 2 wherein said virus is CMV.

3. The method recited in claim 1 wherein said virus is CMV pepo.

4. A method for inhibiting the multiplication of viruses in plants comprising the step of treating said plants with a composition comprising from 1 $\mu$g/ml to 50 mg/ml caramel and a physiologically acceptable diluent, adjuvant or carrier.

5. The method recited in claim 4 wherein said virus is CMV.

6. The method recited in claim 4 wherein said virus is CMV pepo.

7. A solution comprising from 1 $\mu$g/ml to 50 mg/ml caramel and an anti-plant pathogen agent.

8. A solution comprising from 1 $\mu$g/ml to 50 mg/ml caramel and plant fertilizer.

9. The solution recited in claim 7 or 8 wherein said caramel is a glucose caramel.

10. The solution recited in claim 9 wherein said glucose caramel is a Type IV glucose caramel.

* * * * *

UNITED STATES PATENT AND TRADEMARK OFFICE
CERTIFICATE OF CORRECTION

PATENT NO. : 5,304,544

DATED : April 19, 1994

INVENTORS : OHKI et al.

It is certified that error appears in the above-identified patent and that said Letters Patent is hereby corrected as shown below:

column 1, line 8, replace "ore" with --more--;

column 3, line 13, replace "$\geq$" with --$\leq$--;

column 3, line 14, replace "$\geq$" with --$\leq$--;

column 3, line 15, replace "$\geq$" with --$\leq$--;

column 3, line 16, replace "$\geq$" with --$\leq$--; and column 4, line 26, replace "claim 2" with --claim 1--.

Signed and Sealed this

Eighth Day of November, 1994

Attest:

BRUCE LEHMAN

Attesting Officer     Commissioner of Patents and Trademarks